US012564353B2

(12) United States Patent
Kim

(10) Patent No.: US 12,564,353 B2
(45) Date of Patent: Mar. 3, 2026

(54) ELECTRONIC APPARATUS AND METHOD FOR MEASURING SKIN FLUORESCENCE USING ELECTRONIC APPARATUS

(71) Applicant: SAMSUNG ELECTRONICS CO., LTD., Suwon-si (KR)

(72) Inventor: Younggeol Kim, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 299 days.

(21) Appl. No.: 18/129,411

(22) Filed: Mar. 31, 2023

(65) Prior Publication Data

US 2023/0240590 A1    Aug. 3, 2023

Related U.S. Application Data

(63) Continuation of application No. PCT/KR2021/013661, filed on Oct. 6, 2021.

(30) Foreign Application Priority Data

Oct. 7, 2020    (KR) ........................ 10-2020-0129317

(51) Int. Cl.
*A61B 5/00*            (2006.01)
(52) U.S. Cl.
CPC ............ *A61B 5/441* (2013.01); *A61B 5/0071* (2013.01); *A61B 5/0077* (2013.01); *A61B 5/742* (2013.01)
(58) Field of Classification Search
CPC ..... A61B 5/441; A61B 5/0071; A61B 5/0077; A61B 5/742; A61B 5/443; A61B 5/0075; A61B 5/6898; A61B 5/7445
See application file for complete search history.

(56) References Cited

U.S. PATENT DOCUMENTS

| | | | |
|---|---|---|---|
| 6,603,552 B1 | 8/2003 | Cline et al. | |
| 2010/0103250 A1 | 4/2010 | Ishihara | |

(Continued)

FOREIGN PATENT DOCUMENTS

| | | | | |
|---|---|---|---|---|
| CA | 2977116 C | * 10/2020 | .......... | B07C 5/3427 |
| CN | 106073718 A | 11/2016 | | |

(Continued)

OTHER PUBLICATIONS

Machine-generated English translation of KR-20200021708-A (Year: 2025).*

(Continued)

*Primary Examiner* — Pascal M Bui Pho
*Assistant Examiner* — Taylor Deutsch
(74) *Attorney, Agent, or Firm* — Sughrue Mion, PLLC

(57) ABSTRACT

An electronic device includes a first light source, a second light source, a camera, a memory for storing one or more instructions, and a processor configured to execute the one or more instructions to obtain a compensation constant based on a difference between a first brightness corresponding to a first image captured while light of the first light source is emitted to a skin and a second brightness corresponding to a second image captured while light of the second light source is emitted to the skin, obtain a skin visible reflection component caused by the second light source by applying the compensation constant to a third image captured in while light of the first light source is emitted to the skin, and measure fluorescence by removing the obtained skin visible reflection component from a fourth image captured while light of the second light source is emitted to the skin.

20 Claims, 11 Drawing Sheets

(56) References Cited

U.S. PATENT DOCUMENTS

| | | | |
|---|---|---|---|
| 2012/0057145 A1 | 3/2012 | Tunnell et al. | |
| 2013/0253338 A1 | 9/2013 | Kang et al. | |
| 2017/0209050 A1* | 7/2017 | Fengler | G01J 3/10 |
| 2018/0078141 A1 | 3/2018 | Lee et al. | |
| 2018/0214057 A1 | 8/2018 | Schultz et al. | |
| 2019/0385278 A1* | 12/2019 | Valdaitsev | G01N 21/6458 |
| 2020/0112662 A1* | 4/2020 | Sakamoto | H04N 23/73 |

FOREIGN PATENT DOCUMENTS

| | | | |
|---|---|---|---|
| JP | 2002-336187 A | 11/2002 | |
| JP | 2004-478 A | 1/2004 | |
| JP | 2004-290234 A | 10/2004 | |
| JP | 2008-183349 A | 8/2008 | |
| KR | 10-2011-0011009 A | 2/2011 | |
| KR | 10-2013-0106971 A | 10/2013 | |
| KR | 10-2014-0096773 A | 8/2014 | |
| KR | 10-2016-0147585 A | 12/2016 | |
| KR | 10-2018-0032482 A | 3/2018 | |
| KR | 10-2019-0107720 A | 9/2019 | |
| KR | 20200021708 A * | 3/2020 | A61B 1/043 |
| WO | WO-0042910 A1 * | 7/2000 | A61B 1/0646 |

OTHER PUBLICATIONS

Alexey Lihachev et al., "Autofluorescence imaging of basal cell carcinoma by smartphone RGB Camera", Journal of Biomedical Optics, Dec. 11, 2015, (5 pages).

International Search Report (PCT/ISA/210) issued by the International Searching Authority on Jan. 17, 2022 in International Application No. PCT/KR2021/013661.

Written Opinion (PCT/ISA/237) issued by the International Searching Authority on Jan. 17, 2022 in International Application No. PCT/KR2021/013661.

* cited by examiner

Cal_V

~901

Cal_U$_{visible}$

~903

C_Table

~905

1

ELECTRONIC APPARATUS AND METHOD FOR MEASURING SKIN FLUORESCENCE USING ELECTRONIC APPARATUS

CROSS-REFERENCE TO RELATED APPLICATIONS

This application is a bypass continuation of International Application No. PCT/KR2021/013661, filed on Oct. 6, 2021, in the Korean Intellectual Property Receiving Office, which is based on and claims priority to Korean Patent Application No. 10-2020-0129317, filed on Oct. 7, 2020, in the Korean Intellectual Property Office, the disclosures of which are incorporated herein by reference in their entireties.

BACKGROUND

1. Field

The disclosure relates to an electronic device and a method of measuring skin fluorescence in the electronic device.

2. Description of Related Art

As life expectancy increases, diagnosis and care of health conditions are essential considerations. The skin of the human body is exposed to external environments and contains various metabolites and components. The skin may serve as an indication of a health condition. Accordingly, techniques of diagnosing a skin condition in relation to a health condition are widely used.

A skin condition may be diagnosed in various methods, including diagnosis of a skin condition by capturing an image of the skin with light emitted to the skin and then analyzing skin fluorescence in the captured image. The skin fluorescence may be self-generated light from the skin by ultraviolet light emitted to the skin. For example, when a specific component (e.g., protein) in the composition of the skin is irradiated with ultraviolet (UV) light, and its energy is saturated, visible light having a longer wavelength than the irradiated light is emitted, which may be referred to as fluorescence.

Skin fluorescence may be used as information related to various diseases, and various techniques of measuring skin fluorescence have been attempted.

In a related art skin fluorescence measurement method, for example, UV light may be emitted to the skin, skin fluorescence may be detected for a certain period of time using an optical filter that detects a specific wavelength (e.g., a wavelength corresponding to the skin fluorescence) that is longer than the UV light, and the amount of fluorescence may be measured based on a skin fluorescence decrement, relying on the property that the detected skin fluorescence decreases for a certain period of time.

This related art method may have difficulty measuring the amount of fluorescence accurately since the amount of fluorescence may be further reduced even after the certain period of time. This related art method may also increase the manufacture cost of a skin fluorescence measurement device due to the requirement of an UV light source for outputting UV light and an expensive optical filter for detecting skin fluorescence. Therefore, the method may be inefficient.

SUMMARY

Provided are an electronic device and a method of measuring skin fluorescence in the electronic device, which obtain a fluorescence decrement of ultraviolet (UV) light reflected from the skin, obtain a fluorescence reflection distribution by applying the pre-obtained fluorescence decrement of the reflected UV light to a reflection distribution of reflected visible light, and may enable measurement of skin fluorescence without an expensive optical filter.

Further provided are an electronic device and a method of measuring skin fluorescence in the electronic device, which apply a pre-obtained fluorescence decrement of reflected UV light to a reflection distribution of reflected visible light during measurement of skin fluorescence, thereby removing the need for repeating an operation of emitting UV light and measuring a fluorescence decrement for a certain period of time, each time skin fluorescence is measured, and thus may enable fast measurement of skin fluorescence.

Additional aspects will be set forth in part in the description which follows and, in part, will be apparent from the description, or may be learned by practice of the presented embodiments.

According to an aspect of an embodiment, an electronic device may include a first light source, a second light source, a camera, a memory for storing one or more instructions, and a processor configured to execute the one or more instructions to: obtain a compensation constant based on a difference between a first brightness corresponding to a first image captured by the camera while light of the first light source is emitted to a skin and a second brightness corresponding to a second image captured by the camera while light of the second light source is emitted to the skin, obtain a skin visible reflection component caused by the second light source by applying the compensation constant to a third image captured by the camera in while light of the first light source is emitted to the skin, and measure fluorescence by removing the obtained skin visible reflection component from a fourth image captured by the camera while light of the second light source is emitted to the skin.

The first light source may include a visible light source, and the second light source may include a UV light source.

The processor may be further configured to obtain the compensation constant by emitting UV light to the skin by turning on the second light source, emitting visible light to the skin by turning off the second light source and turning on the first light source, obtaining a first skin reflectance map using a first R, G, B reflection distribution of the first image, and obtaining a second skin reflectance map using a second R, G, B reflection distribution of the second image, where the compensation constant is further obtained for each pixel position of the first image based on a difference between the first skin reflectance map and the second skin reflectance map.

The compensation constant may include compensation constant obtained from a table, stored in the memory, associated with a plurality of compensation constants for each pixel position.

The processor may be further configured to measure the fluorescence by turning on the first light source, obtaining the third image by capturing an image of the skin irradiated with visible light, and, after the third image is obtained, turning off the first light source, turning on the second light source, and obtaining the fourth image by capturing an image of the skin irradiated with UV light, where the processor is further configured to obtain the skin visible reflection component caused by the second light source by applying the compensation constant to the third image and where the processor is further configured to measure the fluorescence by removing the skin visible reflection component caused by the second light source from the fourth image.

The compensation constant may be stored in the memory of the electronic device.

The processor may be configured to measure the fluorescence based on a fluorescence measurement request event.

The processor may be configured to diagnose a skin condition based on a fluorescence measurement value.

The electronic device may include a display, and the processor may be configured to control to display to display information indicating a result of diagnosing a skin condition.

According to an aspect of the disclosure, a method of measuring fluorescence may include obtaining a compensation constant based on a difference between a first brightness corresponding to a first image captured while light of a first light source is emitted to a skin and a second brightness to a second image captured while light of a second light source is emitted to the skin, obtaining a skin visible reflection component caused by the second light source by applying the compensation constant to a third image captured while light of from the first light source is emitted to the skin, and measuring fluorescence by removing the obtained skin visible reflection component from a fourth image captured while light of the second light source is emitted to the skin.

The first light source may include a visible light source, and the second light source may include a UV light source.

The obtaining the compensation constant may include emitting UV light to the skin by turning on the second light source, emitting visible light to the skin by turning off the second light source and turning on the first light source, obtaining a first skin reflectance map using a first R, G, B reflection distribution of the first image, and obtaining a second skin reflectance map using a second R, G, B reflection distribution of the second image, where the compensation constant is obtained for each pixel position of the first image based on a difference between the first skin reflectance map and the second skin reflectance map.

The compensation constant may be obtained from a table, stored in a memory, associated with a plurality of compensation constants for each pixel position.

The measuring the fluorescence may include turning on the first light source, obtaining the third image by capturing an image of the skin irradiated with visible light, and after the third image is obtained, turning off the first light source, turning on the second light source, and obtaining the fourth image by capturing an image of the skin irradiated with UV light, where obtaining the skin visible reflection component caused by the second light source includes applying the compensation constant to the third image and measuring the fluorescence further includes removing the skin visible reflection component caused by the second light source from the fourth image.

According to an aspect of the disclosure, a non-transitory computer-readable storage medium may store instructions that when executed by at least one processor, cause the at least one processor to obtain a compensation constant based on a difference between a first brightness corresponding to a first image captured while light of a first light source is emitted to a skin and a second brightness corresponding to a second image captured while light of a second light source is emitted to the skin, obtaining a skin visible reflection component caused by the second light source by applying the compensation constant to a third image captured while light of the first light source is emitted to the skin, and measuring fluorescence by removing the obtained skin vis-ible reflection component from a fourth image captured while light of the second light source is emitted to the skin.

BRIEF DESCRIPTION OF DRAWINGS

The above and other aspects, features, and advantages of certain embodiments of the present disclosure will be more apparent from the following description taken in conjunction with the accompanying drawings, in which.

DETAILED DESCRIPTION

Figure 1:
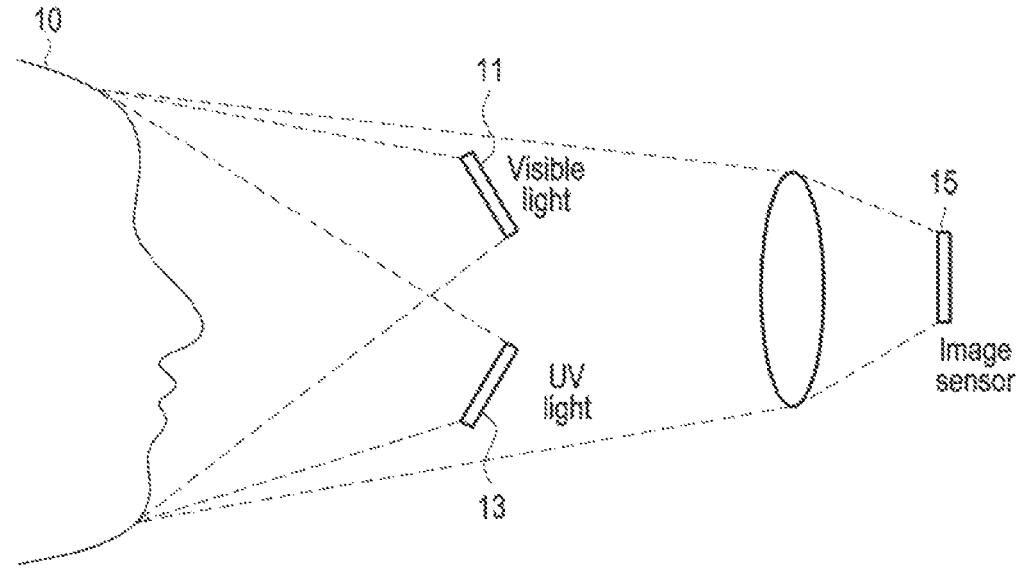
FIG. 1 is a diagram illustrating skin fluorescence measurement according to an embodiment.

Hereinafter, example embodiments of the disclosure will be described in detail with reference to the accompanying drawings. The same reference numerals are used for the same components in the drawings, and redundant descriptions thereof will be omitted. The embodiments described herein are example embodiments, and thus, the disclosure is not limited thereto and may be realized in various other forms. It is to be understood that singular forms include plural referents unless the context clearly dictates otherwise. The terms including technical or scientific terms used in the disclosure may have the same meanings as generally understood by those skilled in the art.

FIG. 1 is a diagram illustrating skin fluorescence measurement according to an embodiment.

Referring to FIG. 1, a skin 10 according to an embodiment may be the skin of various human body parts (e.g. the skin of the face, the skin of a leg, the skin of a hand, and/or the skin of any other body part).

When visible light 11 is emitted to the skin 10, skin visible reflection may occur due to reflection of the visible light 11 emitted to the skin 10.

When ultraviolet (UV) light (e.g., UV ray) 13 is emitted to the skin 10, skin visible reflection may occur due to reflection of the UV light emitted to the skin 10, and fluorescence may be emitted from the skin 10 itself due to the UV light 13 emitted to the skin 10. For example, skin fluorescence may be self-generated light from the skin, caused by the emitted UV light 13, when the UV light 13 is emitted to the skin 10. For example, when the UV light 13 is emitted to the skin 10, a specific component (e.g., protein) in the composition of the skin emits visible light having a longer wavelength than the emitted UV light 13, upon saturation of energy. This may be referred to as fluorescence. According to an embodiment, after the UV light 13 is emitted to the skin, fluorescence may be generated by a specific component (e.g., protein) in the composition of the skin. The amount of fluorescence may decrease for a certain time of period after the generation. According to an embodiment, after the UV light 13 is emitted to the skin 10, an image of the skin to which the UV light 13 is emitted may be captured using an image sensor 15, and a fluorescent component may be obtained from the captured skin image.

Figure 2:
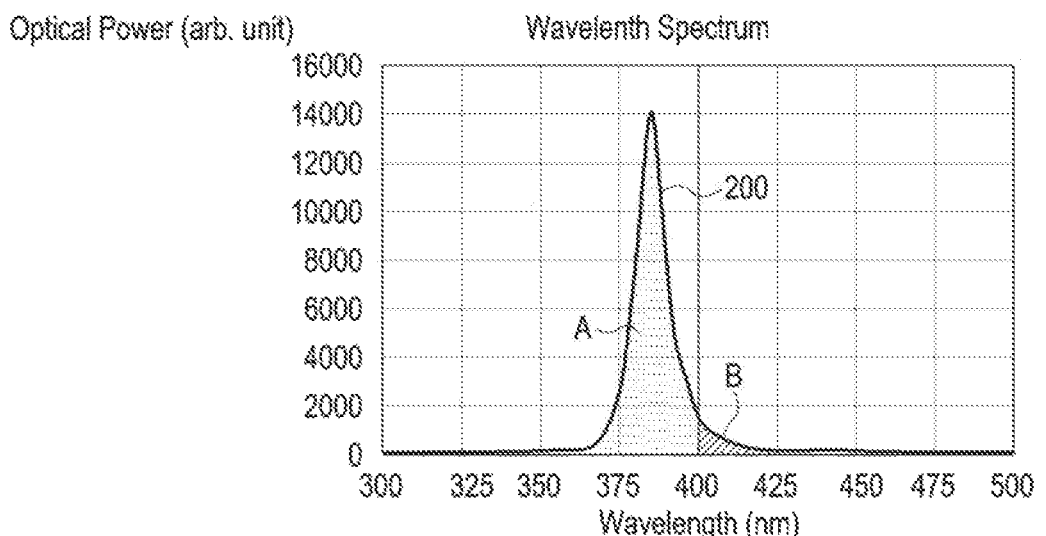
FIG. 2 is a diagram illustrating a wavelength spectrum of ultraviolet (UV) light according to an embodiment.

FIG. 2 is a diagram illustrating a wavelength spectrum of ultraviolet light according to an embodiment.

Referring to FIG. 2, the UV light 13 according to an embodiment may be emitted from a UV light source, and the UV light source may not precisely emit only light in the UV band. For example, a light spectrum 200 emitted from the UV light source may include a light component B in the visible band in addition to a light component A in the UV band. Therefore, reflected light obtained from a captured image of the skin irradiated with light emitted from the UV light source may include not only a fluorescent component from the light component A in the UV band, but also a skin visible reflection component from the light component B in the visible band.

Figure 3A:
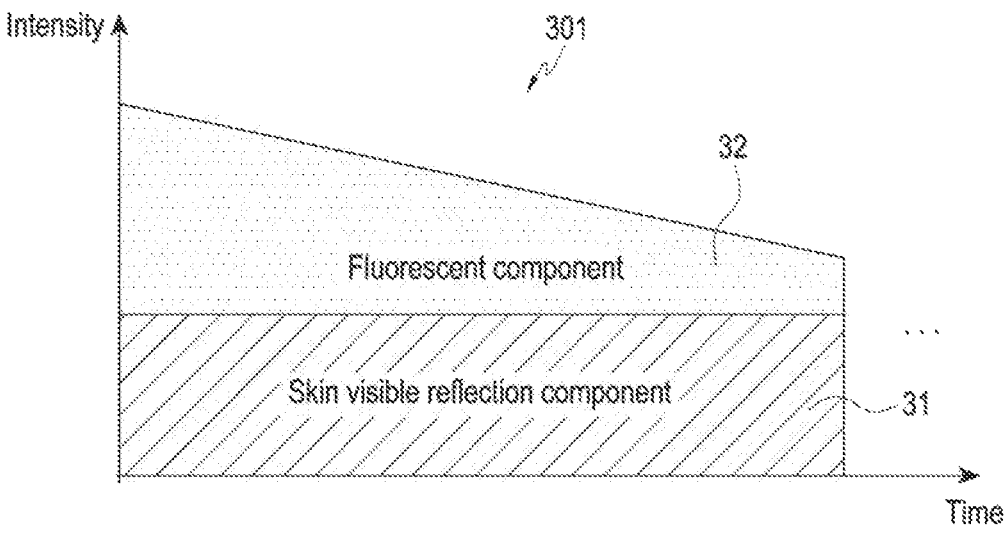
FIG. 3A is a graph showing a fluorescent component and a skin visible reflection component according to an embodiment.

FIG. 3A is a graph showing a fluorescent component and a skin visible reflection component according to an embodiment.

Referring to FIG. 3A, the x axis may represent time, and the y axis may represent light intensities in a graph 301 according to an embodiment. According to an embodiment, the skin visible reflection component 31 may have a constant value over time, whereas a fluorescent component 32 may characteristically decreases over time. The skin visible reflection component 31 is a noise component and may need to be removed to accurately obtain only the fluorescent component 32. According to an embodiment, to reduce the occurrence of the skin visible reflection component 31, a short (e.g., UV cut) filter for removing the light component B in the visible band may be additionally used for the UV light source so that the UV light source may emit only the light component A in the UV band as much as possible.

Figure 3B:
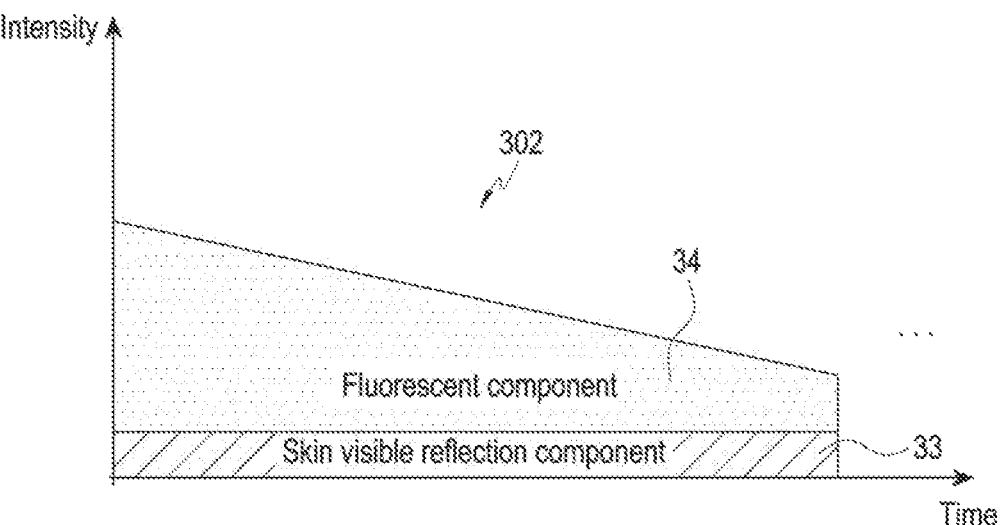
FIG. 3B is a graph showing a fluorescent component and a skin visible reflection component obtained when a short filter is applied to an UV light source according to an embodiment.

FIG. 3B is a graph showing a fluorescent component and a skin visible reflection component obtained when a short filter is applied to an UV light source according to an embodiment.

Referring to FIG. 3B, as shown in graph 302, when the short filter is applied to the UV light source, the amount of a skin visible reflection component 33 is reduced compared to before the short filter is applied according to an embodiment. Therefore, a fluorescent component 34 may be obtained more easily than before the short filter is applied.

However, the above method of obtaining a fluorescent component requires an expensive filter and takes a certain amount of time for each measurement of the fluorescent component, thus consuming much cost and time. According to various embodiments, an electronic device and a method of measuring skin fluorescence in the electronic device may be provided, which may shorten a fluorescent component measurement time without requiring an expensive filter.

Figure 4:
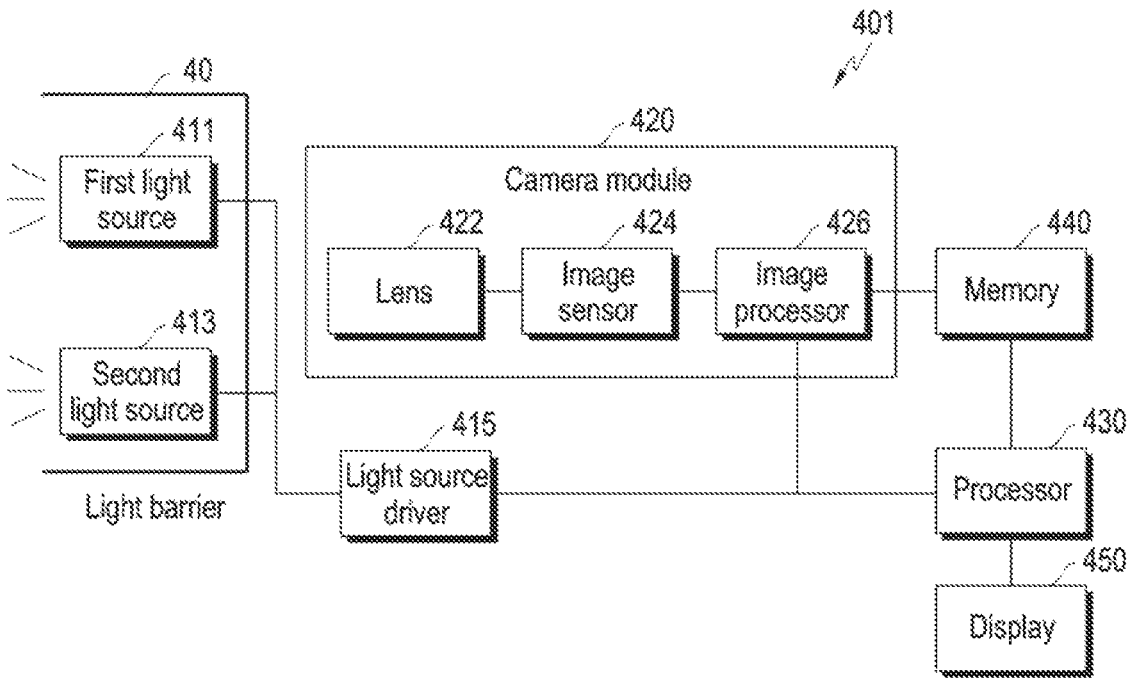
FIG. 4 is a diagram illustrating an electronic device according to an embodiment.

FIG. 4 is a diagram illustrating an electronic device according to an embodiment.

Referring to FIG. 4, an electronic device 401 according to an embodiment may include a first light source 411, a second light source 413, a light source driver 415, a camera module 420, a processor 430, memory 440, and/or a display 450.

The first light source 411 according to an embodiment may include a first light emitting diode (LED) emitting light in the visible band (e.g., a wavelength band of about 400 nm to about 700 nm).

The second light source 413 according to an embodiment may include a second LED emitting light in the UV band (e.g., a wavelength band of about 10 nm to about 400 nm).

A light barrier 40 according to an embodiment may include a barrier wall for blocking the introduction of external light, so that external light other than light from the first light source 411 or the second light source 413 may not be emitted to a subject.

The light source driver 415 according to an embodiment may drive each of the first light source 411 and the second light source 413 and control on/off functions of the first light source 411 and the second light source 413 under the control of the processor 430.

The camera module 420 according to an embodiment may capture a subject (e.g., the skin). According to an embodiment, the camera module 420 may include a lens 422, an image sensor 424, and an image processor 426. According to an embodiment, the image sensor 424 may sense a light component incident through the lens 422, and the image processor 426 may process an image corresponding to the sensed light component and provide the processed image to the processor 430.

The processor 430 according to an embodiment may provide overall control to the components of the electronic device 401. The processor 430 according to an embodiment may obtain compensation constants C (or compensation constant information) for compensating for a brightness difference in each wavelength in a first image captured based on the first light source 411 and a second image captured based on the second light source 413. According to an embodiment, the processor 430 may obtain the compensation constants under the assumption that the first light source 411 and the second light source 413 are identical in terms of the distance between a subject and a light source, an emission angle, and the amount of emitted light. For example, when the same light source is used as the first light source 411 and the second light source 413, an R, G, B reflection distribution from the first light source may match that from the second light source 413, based on which the processor 430 may obtain the compensation constants. According to an embodiment, the processor 430 may obtain one first image (e.g., #Cal_Un) without a fluorescent component, using images captured by emitting UV light to the skin, obtain a second image #Cal_V captured by emitting visible light to the skin, and then obtain a compensation constant (Ci, j) for each pixel position of the image sensor 244 (e.g., every coordinate of an R, G, B sensor) based on a first skin reflectance map using a first R, G, B reflection distribution of the first image and a second skin reflectance map using a second R, G, B reflection distribution of the second image. The processor 430 according to an embodiment may obtain a compensation constant-applied image by applying the compensation constants to a third image captured based on the first light source 411, and predict (calculate or obtain) a skin visible reflection component (e.g., a visible light component that does not include a fluorescent image obtainable under the assumption that second light (e.g., UV light) is emitted to the subject (e.g., the skin) through the second light source 413) using the compensation constant-applied image. The processor 430 according to an embodiment may obtain a fluorescent component by excluding the predicted skin visible reflection component (or visible light component) from a fourth image obtained through the image sensor 424 (e.g., RGB sensor) of the camera module 420 after emitting the second light (e.g., UV light) to the subject (e.g., the skin) through the second light source 413. The processor 430 according to an embodiment may diagnose a skin condition using the obtained fluorescent component.

According to an embodiment, the memory 440 may store at least one command, instructions, and/or data that cause the processor 430 to perform an operation. According to an embodiment, the memory 440 may store the obtained compensation constants and/or the skin reflectance maps.

According to an embodiment, the display 450 may display a screen including an image captured under the control of the processor 430, a fluorescent component obtained from the captured image, and/or information about a skin condition diagnosed using the fluorescent component.

According to an embodiment, the image processor 426 and the processor 430 may be implemented such that one processor performs their functions, or may be configured to subdivide and perform their functions by further including another processor.

According to various embodiments, the electronic device 401 may include the first light source 411, the second light source 413, the camera module 420, the memory 440, and the at least one processor 430 electrically connected to the camera and the memory. The memory may store instructions which when executed, cause the at least one processor to perform obtaining compensation constant information for compensating for a difference between brightness in each wavelength corresponding to a first image captured using the camera while being irradiated by the first light source and brightness in each wavelength corresponding to a second image captured using the camera while being irradiated by the second light source, and obtaining a skin visible reflection component caused by the second light source by applying the compensation constant information to a third image captured while a skin is being irradiated by the first light source, and measuring fluorescence by removing the obtained skin visible reflection component caused by the second light source from a fourth image captured while the skin is being irradiated by the second light source.

According to various embodiments, the first light source may be a visible light source, and the second light source may be a UV light source.

According to various embodiments, obtaining the compensation constant information may include emitting UV light to the skin by turning on the second light source, obtaining the first image without a fluorescent component among captured images of the skin irradiated with the UV light, emitting visible light to the skin by turning off the second light source and turning on the first light source, obtaining the second image being a captured image of the skin irradiated with the visible light, obtaining a first skin reflectance map using a first R, G, B reflection distribution of the first image, obtaining a second skin reflectance map using a second R, G, B reflection distribution of the second image, and obtaining the compensation constant information including a compensation constant for each pixel position of the first image based on a difference between the first skin reflectance map and the second skin reflectance map.

According to various embodiments, the compensation constant may be obtained from a table, stored in the memory, associated with a plurality of the compensation constants for each pixel position.

According to various embodiments, measuring the fluorescent component may include turning on the first light source and obtaining the third image by capturing an image of the skin irradiated with visible light using the camera according to an activation of the first light source, turning off the first light source, turning on the second light source, and obtaining the fourth image by capturing an image of the skin irradiated with UV light using the camera according to the activation of the second light source, after the third image is obtained, obtaining the skin visible reflection component caused by the second light source associated with the fourth image by applying the compensation constant information to the third image, and measuring the fluorescence by removing the skin visible reflection component caused by the second light source from the fourth image.

According to various embodiments, the compensation constant may be stored in the memory.

According to various embodiments, measuring the fluorescence may be performed based on a fluorescence measurement request event.

According to various embodiments, the processor may be configured to perform diagnosing a skin condition based on a fluorescence measurement value.

According to various embodiments, the electronic device may further include a display, and the processor may be configured to control to display information indicating a result of diagnosing a skin condition on the display.

Figure 5:
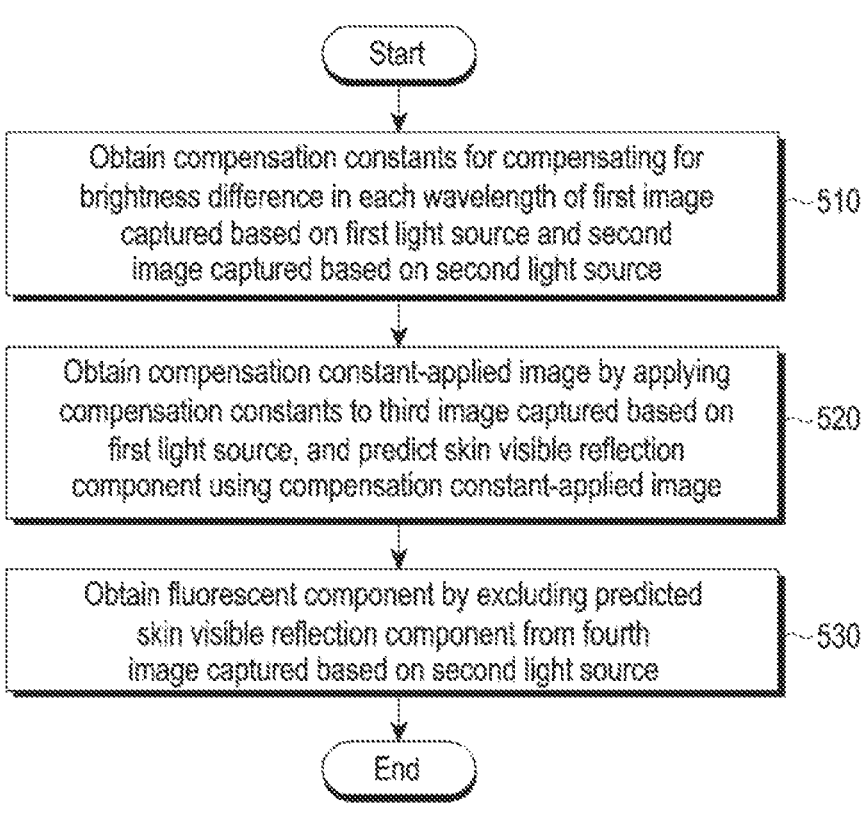
FIG. 5 is a flowchart illustrating a fluorescence measurement method in an electronic device according to an embodiment.

FIG. 5 is a flowchart illustrating a fluorescence measurement method in an electronic device according to an embodiment.

Referring to FIG. 5, the processor 430 of the electronic device 401 according to an embodiment may perform at least one of operations 510 to 530.

In operation 510, the processor 430 according to an embodiment may obtain compensation constants C for compensating for a bright difference in each wavelength in a first image captured based on the first light source 411 and a second image captured based on the second light source 413. According to an embodiment, the processor 430 may obtain the compensation constants under the assumption that the first light source 411 and the second light source 413 are identical in terms of the distance between a subject and a light source, an emission angle, and the amount of emitted light. For example, when the same light source is used as the first light source 411 and the second light source 413, an R, G, B reflection distribution from the first light source may match that from the second light source 413, based on which the processor 430 may obtain the compensation constants. According to an embodiment, the processor 430 may obtain one first image (e.g., #Cal_Un) without a fluorescent component, using images captured by emitting UV light to the skin, obtain a second image #Cal_V captured by emitting visible light to the skin, and then obtain a compensation constant $(C_i, j)$ for each pixel position of the image sensor 244 (e.g., every coordinate of the R, G, B sensor) based on a first skin reflectance map using a first R, G, B reflection distribution of the first image and a second skin reflectance map using a second R, G, B reflection distribution of the second image.

For example, the skin reflectance maps may be generated (or obtained) as in Equation (1).

$$UVn*Rfn(I,j)=Cn*VSLn*Rfn(I,j) \qquad (1)$$

In Equation (1), $Rf_n(I,j)$ may be a reference skin reflectance map obtained from pixels at positions I,j of the image sensor 424, $UV_n*Rf_n(I,j)$ may be the first skin reflectance map, $VSL_n*Rf_n(I,j)$ may be the second skin reflectance map, $VSL_n$ may be a first light component, UVn may be a second light component, and Cn may be a constant for compensating for the brightness difference in each wavelength in first light and second light.

In operation 520, the processor 430 according to an embodiment may obtain a compensation constant-applied image by applying the compensation constants to a third image captured based on the first light source 411, and predict (calculate or obtain) a skin visible reflection component (e.g., a visible light component that does not include a fluorescent image obtainable under the assumption that second light (e.g., UV light) is emitted to the subject (e.g., the skin) through the second light source 413) using the compensation constant-applied image.

In operation 530, the processor 430 according to an embodiment may obtain a fluorescent component by excluding the predicted skin visible reflection component (or visible light component) from a fourth image obtained through the image sensor 424 (e.g., RGB sensor) of the camera module 420 after emitting the second light (e.g., UV light) to the subject (e.g., the skin) through the second light source 413. The processor 430 according to an embodiment may diagnose a skin condition using the obtained fluorescent component.

Figure 6:
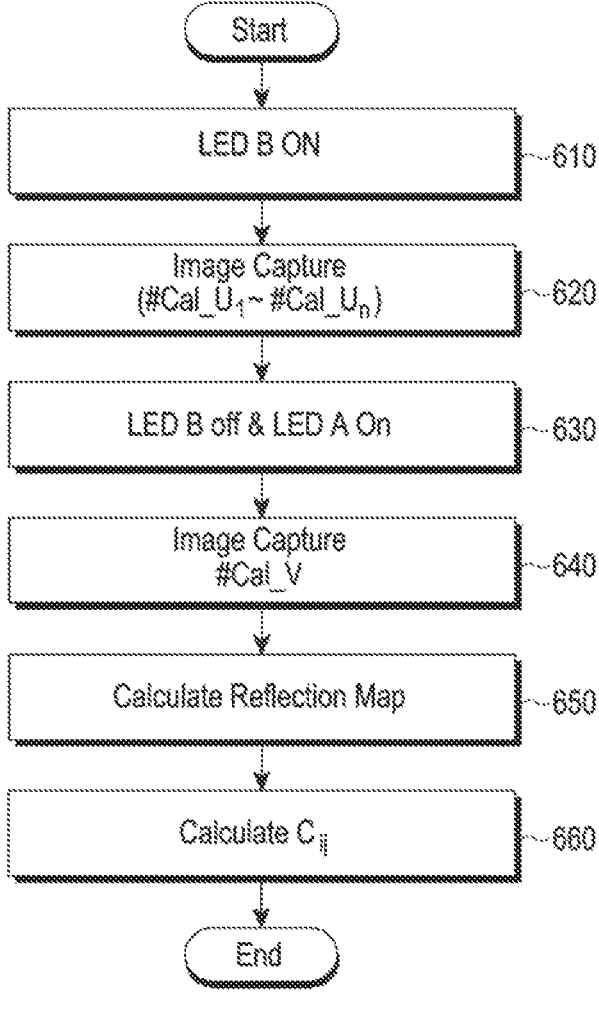
FIG. 6 is a flowchart illustrating a method of obtaining a compensation constant for each pixel position of an image captured by visible light and an image captured by UV light in an electronic device according to an embodiment.

FIG. 6 is a flowchart illustrating a method of obtaining a compensation constant for each pixel position of an image captured by visible light and an image captured by UV light in an electronic device according to an embodiment.

Referring to FIG. 6, the processor 430 of the electronic device 401 according to an embodiment may perform at least one of operations 610 to 660.

In operation 610, the processor 430 according to an embodiment may turn on LED B (e.g., the second light source 413) (LED B ON). According to an embodiment, as LED B is turned on, UV light from LED B may be emitted to the skin.

In operation 620, the processor 430 according to an embodiment may obtain a first image #Cal_Un by capturing the skin irradiated with UV light for or after a specified time (image capture #Cal_U1 to #Cal_Un). According to an embodiment, the processor 430 may obtain a plurality of images #Cal_U1 to #Cal_Un by capturing the skin a plurality of times until fluorescence emitted from the emission of the UV light to the skin gradually decreases and the emission stops, and may obtain the first image (e.g., #Cal_Un) having no fluorescent component among the plurality of images. According to an embodiment, the processor 430 may wait until the fluorescence emitted from the radiation of the UV light to the skin gradually decreases and the emission finally stops, and then obtain one first image (e.g., #Cal_Un) having no fluorescent component. For example, the first image without the fluorescent component may have a first R, G, B reflection distribution caused by the UV light.

In operation 630, the processor 430 according to an embodiment may turn off LED B (e.g., the second light source 413) and turn on LED A (e.g., the first light source 411) (LED B OFF & LED A ON). According to an embodiment, as LED A is turned on, visible light from LED A may be emitted to the skin.

In operation 640, the processor 430 according to an embodiment may obtain a second image #Cal_V by capturing the skin irradiated with visible light (image capture #Cal_V). The second image according to an embodiment may have a second R, G, B reflection distribution caused by the visible light.

In operation 650, the processor 430 according to an embodiment may obtain a first skin reflectance map by using the first R, G, B reflection distribution of the first image, and obtain a second skin reflectance map by using the second R, G, B reflection distribution of the second image.

In operation 660, the processor 430 according to an embodiment may obtain a compensation constant (Ci,j) for each pixel position of the image sensor 244 (e.g., every coordinate of the R, G, B sensor) by using the first skin reflectance map and the second skin reflectance map. According to an embodiment, the processor 430 may store a table of the compensation constant for each pixel position of the image sensor 244 in the memory 240.

Figure 7:
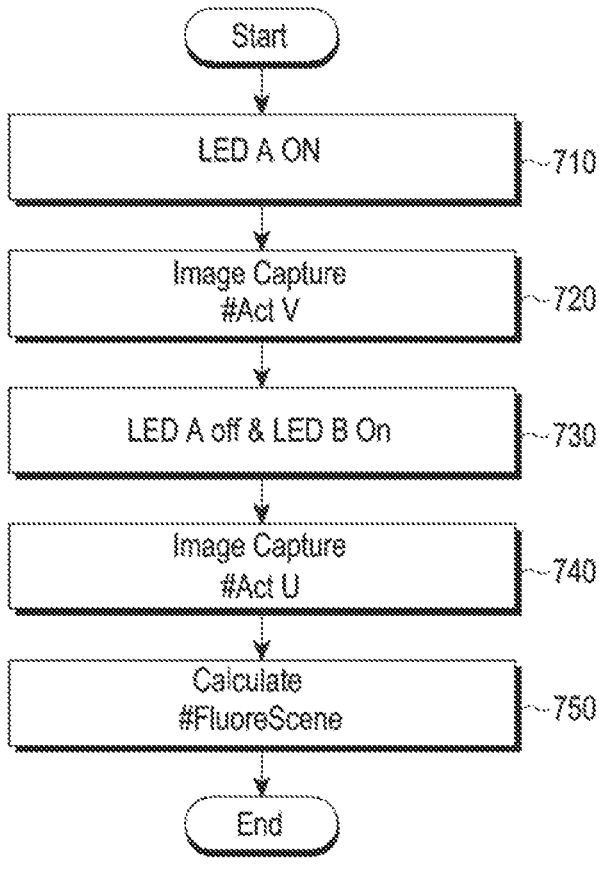
FIG. 7 is a flowchart illustrating a fluorescence measurement method using compensation constants in an electronic device according to an embodiment.

FIG. 7 is a flowchart illustrating a fluorescence measurement method using compensation constants in an electronic device according to an embodiment.

Referring to FIG. 7, the processor 430 of the electronic device 401 according to an embodiment may perform at least one of operations 710 to 750.

In operation 710, the processor 430 according to an embodiment may turn on LED A (e.g., the first light source 411) for fluorescence measurement (LED A ON). According to an embodiment, as LED A is turned on, visible light from LED A may be emitted to the skin. According to an embodiment, the processor 430 may turn on LED A according to a fluorescence measurement request event (a user input or occurrence of a specific event).

In operation 720, the processor 430 according to an embodiment may obtain a third image #Act_V by capturing the skin irradiated with the visible light (image capture #Act_V).

In operation 730, the processor 430 according to an embodiment may turn off LED A (e.g., the first light source 411) and turn on LED B (e.g., the second light source 413) (LED A OFF & LED B ON). According to an embodiment, as LED B is turned on, UV light from LED B may be emitted to the skin.

In operation 740, the processor 430 according to an embodiment may obtain a fourth image #Act_U by capturing the skin irradiated with the UV light (image capture #Act_U).

In operation 750, the processor 430 according to an embodiment may predict a visible light component without a fluorescent component in the fourth image #Act_U by applying compensation constants to the third image, and measure fluorescence (or obtain a fluorescent component or obtain a fluorescent image FS_img) by excluding the predicted visible light component in the fourth image #Act_U. The processor 430 according to an embodiment may diagnose a skin condition using the obtained fluorescent component.

According to various embodiments, a method of measuring fluorescence in an electronic device may include obtaining compensation constant information for compensating for a difference between brightness in each wavelength corresponding to a first image captured using the camera while being irradiated by the first light source and brightness in each wavelength corresponding to a second image captured using the camera while being irradiated by the second light source, obtaining a skin visible reflection component caused by the second light source by applying the compensation constant information to a third image captured while a skin is irradiated by the first light source, and measuring fluorescence by removing the obtained skin visible reflection component caused by the second light source from a fourth image captured while the skin is irradiated by the second light source.

According to various embodiments, the first light source may be a visible light source, and the second light source may be an UV light source.

According to various embodiments, obtaining the compensation constant information may include emitting UV light to the skin by turning on the second light source, obtaining the first image without a fluorescent component among captured images of the skin irradiated with the UV light, emitting visible light to the skin by turning off the second light source and turning on the first light source, obtaining the second image being a captured image of the skin irradiated with the visible light, obtaining a first skin reflectance map using a first R, G, B reflection distribution of the first image, obtaining a second skin reflectance map using a second R, G, B reflection distribution of the second image, and obtaining the compensation constant information including a compensation constant for each pixel position of the first image based on a difference between the first skin reflectance map and the second skin reflectance map.

According to various embodiments, the compensation constant may be obtained from a table, stored in a memory, associated with a plurality of compensation constants for each pixel position.

According to various embodiments, measuring the fluorescent component may include turning on the first light source, and obtaining the third image by capturing an image of the skin irradiated with visible light using the camera according to the activation of the first light source, turning off the first light source, turning on the second light source, and obtaining the fourth image by capturing an image of the skin irradiated with UV light using the camera according to the activation of the second light source, after the third image is obtained, obtaining the skin visible reflection component caused by the second light source associated with the fourth image by applying the compensation constant information to the third image, and measuring the fluorescence by removing the skin visible reflection component caused by the second light source from the fourth image.

According to various embodiments, the method may include storing the compensation constants in the memory.

According to various embodiments, the method may include receiving a fluorescence measurement request event.

According to various embodiments, the method may include diagnosing a skin condition based on a fluorescence measurement value.

According to various embodiments, the method may include displaying information indicating a result of diagnosing the skin condition on the display.

Figure 8:
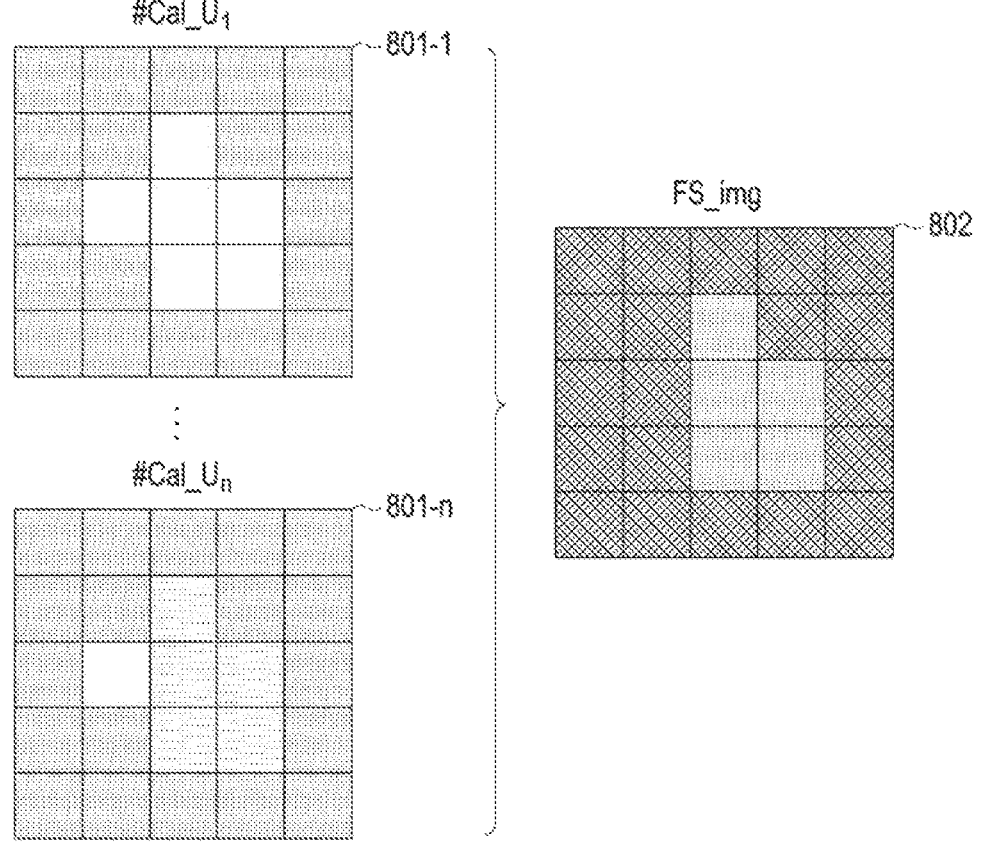
FIG. 8 is a diagram illustrating captured images of the skin irradiated with UV light, and a fluorescent image according to an embodiment.

FIG. 8 is a diagram illustrating captured images of the skin irradiated with UV light, and a fluorescent image according to an embodiment.

Referring to FIG. 8, when UV light is emitted to the skin, the electronic device 401 according to an embodiment may capture an image of the skin. The electronic device 401 may obtain a plurality of images #Cal_U1 to #Cal_Un 801-1 to 801-$n$ by capturing the skin a plurality of times until fluorescence emitted from the emission of the UV light to the skin gradually decreases and then stops, and obtain a fluorescent image FS_image 802 by calculating the difference between the initial image #Cal_U1 having the largest fluorescent component and the image #Cal_Un in which the fluorescent component decreases to 0 among the plurality of images #Cal_U1 to #Cal_Un 801-1 to 801-$n$.

Figure 9:
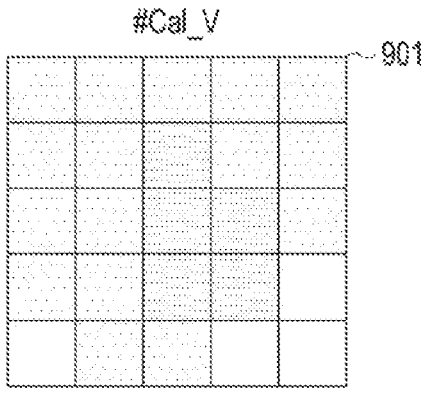
FIG. 9 is a diagram illustrating a captured image of the skin irradiated with visible light, an image obtained by excluding a florescent component in a captured image of the skin irradiated with UV light, and a table of compensation constants for the respective pixel positions of an image, according to an embodiment
Figure 9:
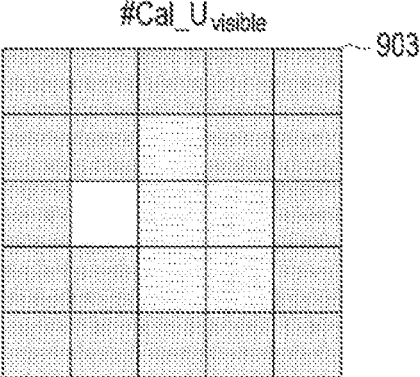
Figure 9:
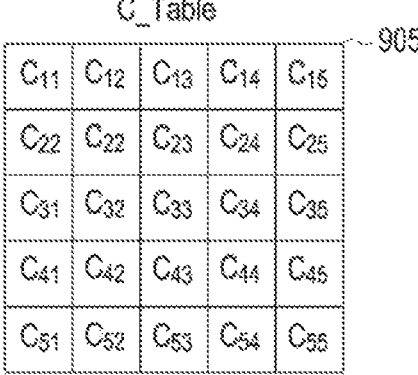

FIG. 9 is a diagram illustrating a captured image of the skin irradiated with visible light, an image obtained by excluding a florescent component in a captured image of the skin irradiated with UV light, and a table of compensation constants for the respective pixel positions of an image, according to an embodiment.

Referring to FIG. 9, the electronic device 401 according to an embodiment may obtain a captured image #cal_V (e.g., a second image) 901 of the skin irradiated with visible light, and obtain an image #cal_Uvisible (e.g., a first image) 903 by excluding a fluorescent component from a captured image #cal_U of the skin irradiated with UV light. The electronic device 401 according to an embodiment may obtain a first skin reflectance map by using a first R, G, B reflection distribution of the first image 901, obtain a second skin reflectance map of the second image 903, and obtain a compensation constant (Ci,j) for each pixel position of the image sensor 244 (e.g., every coordinate of the R, G, B sensor) using the first skin reflectance map and the second skin reflectance map, thereby obtaining a table C_table 905 of the compensation constants for the respective pixel positions of the image sensor 244.

Figure 10:
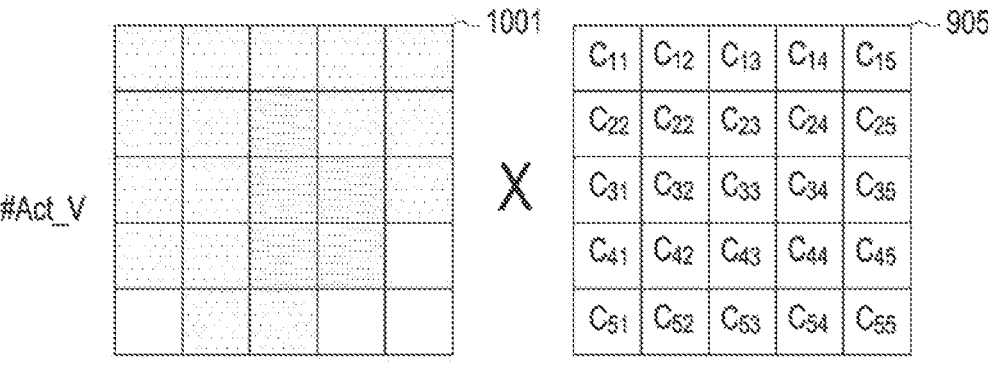
FIG. 10 is a diagram illustrating a captured image of the skin irradiated with visible light, an image obtained by excluding a fluorescent component in a captured image of the skin irradiated with UV light, and a table of compensation constants for the respective pixel positions of an image, after fluorescence measurement starts, according to an embodiment.
Figure 10:
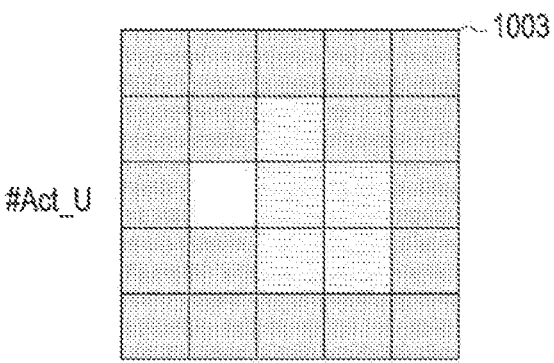
Figure 10:
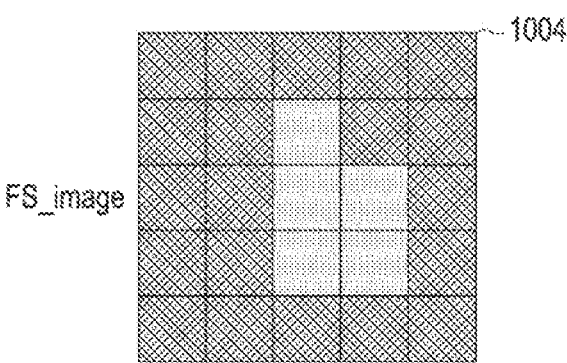

FIG. 10 is a diagram illustrating a captured image of the skin irradiated with visible light, an image obtained by excluding a fluorescent component in a captured image of the skin irradiated with UV light, and a table of compensation constants for the respective pixel positions of an image, after fluorescence measurement starts, according to an embodiment.

Referring to FIG. 10, the electronic device 401 according to an embodiment may obtain a third image #Act_V 1001 by capturing the skin irradiated with visible light, and predict a visible light component #Act_U 1003 without a fluorescent component in a fourth image by applying the pixel position-wise compensation constant table C_table 905 to the third image #Act_V. The electronic device 401 according to an embodiment may measure fluorescence (or obtain the fluorescent component or obtain a fluorescent image FS_img 1004) by excluding the predicted visible light component #Act_U 1003 from the fourth image.

According to various embodiments, as a fluorescence decrement of ultraviolet light reflected from the skin is obtained and a fluorescence reflection distribution is obtained by applying the pre-obtained fluorescence decrement of the reflected ultraviolet light to a reflection distribution of reflected visible light, skin fluorescence may be measured without an expensive optical filter.

According to various embodiments, when ski fluorescence is measured, a pre-obtained fluorescence decrement of reflected ultraviolet light is applied to a reflection distribution of reflected visible light. Therefore, there is no need for repeating an operation of irradiating ultraviolet light and measuring a fluorescence decrement for a certain period of time, each time skin fluorescence is measured, and thus skin fluorescence may be measured rapidly.

An electronic device (e.g., the electronic device 401 of FIG. 4) according to various embodiments will be described below.

Figure 11:
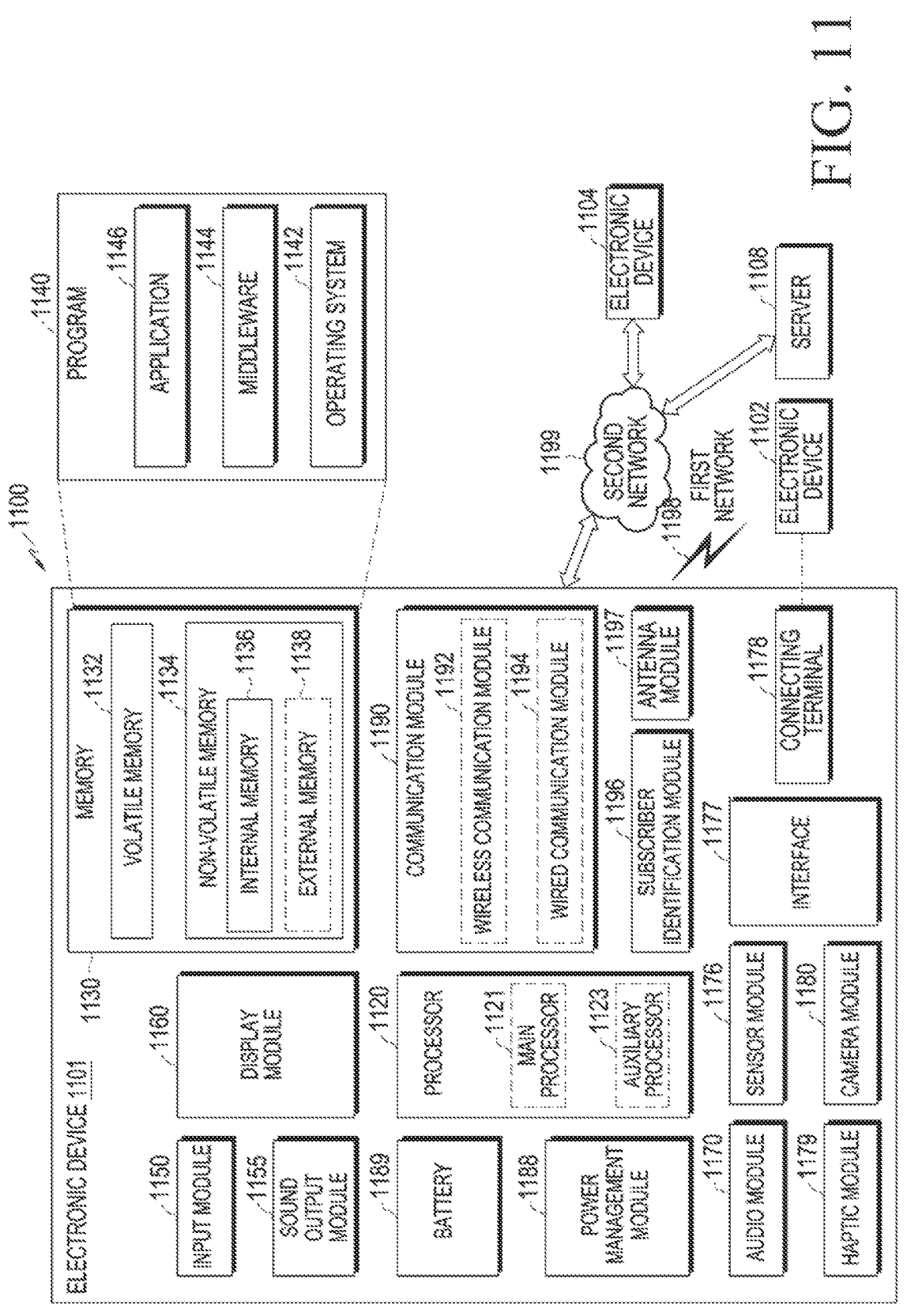
FIG. 11 is a diagram illustrating an electronic device in a network environment according to various embodiments.

FIG. 11 is a diagram illustrating an electronic device 1101 in a network environment 1100 according to various embodiments.

Referring to FIG. 11, the electronic device 1101 in the network environment 1100 may communicate with an electronic device 1102 via a first network 1198 (e.g., a short-range wireless communication network), or at least one of an electronic device 1104 or a server 1108 via a second network 1199 (e.g., a long-range wireless communication network). According to an embodiment, the electronic device 1101 may communicate with the electronic device 1104 via the server 1108. According to an embodiment, the electronic device 1101 may include a processor 1120, memory 1130, an input module 1150, a sound output module 1155, a display module 1160, an audio module 1170, a sensor module 1176, an interface 1177, a connecting terminal 1178, a haptic module 1179, a camera module 1180, a power management module 1188, a battery 1189, a communication module 1190, a subscriber identification module (SIM) 1196, or an antenna module 1197. In some embodiments, at least one of the components (e.g., the connecting terminal 1178) may be omitted from the electronic device 1101, or one or more other components may be added in the electronic device 1101. In some embodiments, some of the components (e.g., the sensor module 1176, the camera module 1180, or the antenna module 1197) may be implemented as a single component (e.g., the display module 1160).

The processor 1120 may execute, for example, software (e.g., a program 1140) to control at least one other component (e.g., a hardware or software component) of the electronic device 1101 coupled with the processor 1120, and may perform various data processing or computation. According to one embodiment, as at least part of the data processing or computation, the processor 1120 may store a command or data received from another component (e.g., the sensor module 1176 or the communication module 1190) in volatile memory 1132, process the command or the data stored in the volatile memory 1132, and store resulting data in non-volatile memory 1134. According to an embodiment, the processor 1120 may include a main processor 1121 (e.g., a central processing unit (CPU) or an application processor (AP)), or an auxiliary processor 1123 (e.g., a graphics processing unit (GPU), a neural processing unit (NPU), an image signal processor (ISP), a sensor hub processor, or a communication processor (CP)) that is operable independently from, or in conjunction with, the main processor 1121. For example, when the electronic device 1101 includes the main processor 1121 and the auxiliary processor 1123, the auxiliary processor 1123 may be adapted to consume less power than the main processor 1121, or to be specific to a specified function. The auxiliary processor 1123 may be implemented as separate from, or as part of the main processor 1121.

The auxiliary processor 1123 may control at least some of functions or states related to at least one component (e.g., the display module 1160, the sensor module 1176, or the communication module 1190) among the components of the electronic device 1101, instead of the main processor 1121 while the main processor 1121 is in an inactive (e.g., sleep) state, or together with the main processor 1121 while the main processor 1121 is in an active state (e.g., executing an application). According to an embodiment, the auxiliary processor 1123 (e.g., an image signal processor or a communication processor) may be implemented as part of another component (e.g., the camera module 1180 or the communication module 1190) functionally related to the auxiliary processor 1123. According to an embodiment, the auxiliary processor 1123 (e.g., the neural processing unit) may include a hardware structure specified for artificial intelligence model processing. An artificial intelligence model may be generated by machine learning. Such learning may be performed, e.g., by the electronic device 1101 where the artificial intelligence is performed or via a separate server (e.g., the server 1108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 1130 may store various data used by at least one component (e.g., the processor 1120 or the sensor module 1176) of the electronic device 1101. The various data may include, for example, software (e.g., the program 1140) and input data or output data for a command related thererto. The memory 1130 may include the volatile memory 1132 or the non-volatile memory 1134.

The program 1140 may be stored in the memory 1130 as software, and may include, for example, an operating system (OS) 1142, middleware 1144, or an application 1146.

The input module 1150 may receive a command or data to be used by another component (e.g., the processor 1120) of the electronic device 1101, from the outside (e.g., a user) of the electronic device 1101. The input module 1150 may include, for example, a microphone, a mouse, a keyboard, a key (e.g., a button), or a digital pen (e.g., a stylus pen).

The sound output module 1155 may output sound signals to the outside of the electronic device 1101. The sound output module 1155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 1160 may visually provide information to the outside (e.g., a user) of the electronic device 1101. The display module 1160 may include, for example, a display, a hologram device, or a projector and control circuitry to control a corresponding one of the display, hologram device, and projector. According to an embodiment, the display module 1160 may include a touch sensor adapted to detect a touch, or a pressure sensor adapted to measure the intensity of force incurred by the touch.

The audio module 1170 may convert a sound into an electrical signal and vice versa. According to an embodiment, the audio module 1170 may obtain the sound via the input module 1150, or output the sound via the sound output module 1155 or a headphone of an external electronic device (e.g., an electronic device 1102) directly (e.g., wiredly) or wirelessly coupled with the electronic device 1101.

The sensor module 1176 may detect an operational state (e.g., power or temperature) of the electronic device 1101 or an environmental state (e.g., a state of a user) external to the electronic device 1101, and then generate an electrical signal or data value corresponding to the detected state. According to an embodiment, the sensor module 1176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1177 may support one or more specified protocols to be used for the electronic device 1101 to be coupled with the external electronic device (e.g., the electronic device 1102) directly (e.g., wiredly) or wirelessly. According to an embodiment, the interface 1177 may include, for example, a high definition multimedia interface (HDMI), a universal serial bus (USB) interface, a secure digital (SD) card interface, or an audio interface.

A connecting terminal 1178 may include a connector via which the electronic device 1101 may be physically connected with the external electronic device (e.g., the electronic device 1102). According to an embodiment, the connecting terminal 1178 may include, for example, a HDMI connector, a USB connector, a SD card connector, or an audio connector (e.g., a headphone connector).

The haptic module 1179 may convert an electrical signal into a mechanical stimulus (e.g., a vibration or a movement) or electrical stimulus which may be recognized by a user via his tactile sensation or kinesthetic sensation. According to an embodiment, the haptic module 1179 may include, for example, a motor, a piezoelectric element, or an electric stimulator.

The camera module 1180 may capture a still image or moving images. According to an embodiment, the camera module 1180 may include one or more lenses, image sensors, image signal processors, or flashes.

The power management module 1188 may manage power supplied to the electronic device 1101. According to one embodiment, the power management module 1188 may be implemented as at least part of, for example, a power management integrated circuit (PMIC).

The battery 1189 may supply power to at least one component of the electronic device 1101. According to an embodiment, the battery 1189 may include, for example, a primary cell which is not rechargeable, a secondary cell which is rechargeable, or a fuel cell.

The communication module 1190 may support establishing a direct (e.g., wired) communication channel or a wireless communication channel between the electronic device 1101 and the external electronic device (e.g., the electronic device 1102, the electronic device 1104, or the server 1108) and performing communication via the established communication channel. The communication module 1190 may include one or more communication processors that are operable independently from the processor 1120 (e.g., the AP) and supports a direct (e.g., wired) communication or a wireless communication. According to an embodiment, the communication module 1190 may include a wireless communication module 1192 (e.g., a cellular communication module, a short-range wireless communication module, or a global navigation satellite system (GNSS) communication module) or a wired communication module 1194 (e.g., a local area network (LAN) communication module or a power line communication (PLC) module). A corresponding one of these communication modules may communicate with the external electronic device via the first network 1198 (e.g., a short-range communication network, such as Bluetooth™, wireless-fidelity (Wi-Fi) direct, or infrared data association (IrDA)) or the second network 1199 (e.g., a long-range communication network, such as a legacy cellular network, a 5$^{th}$ generation (5G) network, a next-generation communication network, the Internet, or a computer network (e.g., LAN or wide area network (WAN))).

These various types of communication modules may be implemented as a single component (e.g., a single chip), or may be implemented as multi components (e.g., multi chips) separate from each other. The wireless communication module 1192 may identify and authenticate the electronic device 1101 in a communication network, such as the first network 1198 or the second network 1199, using subscriber information (e.g., international mobile subscriber identity (IMSI)) stored in the subscriber identification module 1196.

The wireless communication module 1192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 1192 may support a high-frequency band (e.g., the mmWave band) to achieve, e.g., a high data transmission rate. The wireless communication module 1192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 1192 may support various requirements specified in the electronic device 1101, an external electronic device (e.g., the electronic device 1104), or a network system (e.g., the second network 1199). According to an embodiment, the wireless communication module 1192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 1197 may transmit or receive a signal or power to or from the outside (e.g., the external electronic device) of the electronic device 1101. According to an embodiment, the antenna module 1197 may include an antenna including a radiating element composed of a conductive material or a conductive pattern formed in or on a substrate (e.g., a printed circuit board (PCB)). According to an embodiment, the antenna module 1197 may include a plurality of antennas (e.g., array antennas). In such a case, at least one antenna appropriate for a communication scheme used in the communication network, such as the first network 1198 or the second network 1199, may be selected, for example, by the communication module 1190 (e.g., the wireless communication module 1192) from the plurality of antennas. The signal or the power may then be transmitted or received between the communication module 1190 and the external electronic device via the selected at least one antenna. According to an embodiment, another component (e.g., a radio frequency integrated circuit (RFIC)) other than the radiating element may be additionally formed as part of the antenna module 1197.

According to various embodiments, the antenna module 1197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 1101 and the external electronic device 1104 via the server 1108 coupled with the second network 1199. Each of the electronic devices 1102 or 1104 may be a device of a same type as, or a different type, from the electronic device 1101. According to an embodiment, all or some of operations to be executed at the electronic device 1101 may be executed at one or more of the external electronic devices 1102, 1104, or 1108. For example, if the electronic device 1101 should perform a function or a service automatically, or in response to a request from a user or another device, the electronic device 1101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1101. The electronic device 1101 may provide the outcome, with or without further processing of the outcome, as at least part of a reply to the request. To that end, a cloud computing, distributed computing, mobile edge computing (MEC), or client-server computing technology may be used, for example. The electronic device 1101 may provide ultra low-latency services using, e.g., distributed computing or mobile edge computing. In another embodiment, the external electronic device 1104 may include an internet-of-things (IoT) device. The server 1108 may be an intelligent server using machine learning and/or a neural network. According to an embodiment, the external electronic device 1104 or the server 1108 may be included in the second network 1199. The electronic device 1101 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B", "at least one of A and B", "at least one of A or B", "A, B, or C", "at least one of A, B, and C", and "at least one of A, B, or C", may include any one of, or all possible combinations of the items enumerated together in a corresponding one of the phrases. As used herein, such terms as "1st" and "2nd", or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with", "coupled to", "connected with", or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, logic, logic block, part, or circuitry. A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 1140) including one or more instructions that are stored in a storage medium (e.g., internal memory 1136 or external memory 1138) that is readable by a machine (e.g., the electronic device 1101). For example, a processor (e.g., the processor 1120) of the machine (e.g., the electronic device 1101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to various embodiments, in a non-volatile storage medium storing instructions, the instructions may be configured to, when executed by at least one processor, cause the at least one processor to perform at least one operation. The at least one operation may include obtaining compensation constant information for compensating for a difference between brightness in each wavelength corresponding to a first image captured using the camera in a state of irradiation from the first light source and brightness in each wavelength corresponding to a second image captured using the camera in a state of irradiation from the second light source, obtaining a skin visible reflection component caused by the second light source by applying the compensation constant information to a third image captured in a state of irradiation to a skin from the first light source, and measuring fluorescence by removing the obtained skin visible reflection component caused by the second light source from a fourth image captured in a state of irradiation to the skin from the second light source.

The embodiments of the disclosure disclosed in the specification and the drawings provide merely specific examples to easily describe technical content according to the embodiments of the disclosure and help the understanding of the embodiments of the disclosure, not intended to limit the scope of the embodiments of the disclosure. Accordingly, the scope of various embodiments of the disclosure should be interpreted as encompassing all modifications or variations derived based on the technical spirit of various embodiments of the disclosure in addition to the embodiments disclosed herein.

What is claimed is:
1. An electronic device comprising:
a first light source;
a second light source;
a camera;
memory storing instructions; and
a processor,
wherein the instructions, when executed by the processor, cause the electronic device to:
obtain a compensation constant based on a difference between a first brightness corresponding to a first image captured using the camera while light of the first light source is emitted to a skin and a second brightness corresponding to a second image captured using the camera while light of the second light source is emitted to the skin;
apply the compensation constant to a third image captured using the camera while light of the first light source is emitted to the skin,
based on the third image to which the compensation constant is applied, obtain a skin visible reflection component associated with an image which is captured using the camera while light of the second light source is emitted to the skin, the skin visible reflection component corresponding to a light component in the visible band that is emitted in addition to a light component in the ultraviolet (UV) band that is emitted while the light of the second light source is emitted to the skin, and measure fluorescence by removing the skin visible reflection component from a fourth image captured using the camera while light of the second light source is emitted to the skin.

2. The electronic device of claim 1, wherein the first light source comprises a visible light source, and
wherein the second light source comprises a UV light source.

3. The electronic device of claim 1, wherein the instructions, when executed by the processor, cause the electronic device to obtain the compensation constant by:
emitting UV light to the skin by turning on the second light source;
emitting visible light to the skin by turning off the second light source and turning on the first light source;
obtaining a first skin reflectance map using a first R, G, B reflection distribution of the first image; and
obtaining a second skin reflectance map using a second R, G, B reflection distribution of the second image, and
wherein the compensation constant is further obtained for each pixel position of the first image based on a difference between the first skin reflectance map and the second skin reflectance map.

4. The electronic device of claim 3, wherein the compensation constant is obtained from a table, stored in the memory, associated with a plurality of compensation constants for each pixel position.

5. The electronic device of claim 1, wherein the instructions, when executed by the processor, cause the electronic device to measure the fluorescence by:
turning on the first light source,
obtaining the third image by capturing an image of the skin irradiated with visible light emitted by the first light source using the camera; and
after the third image is obtained:
turning off the first light source,
turning on the second light source, and
obtaining the fourth image by capturing an image of the skin irradiated with UV light emitted by the second light source using the camera,
wherein the instructions, when executed by the processor, cause the electronic device to obtain the skin visible reflection component caused by the second light source by applying the compensation constant to the third image, and
wherein the instructions, when executed by the processor, cause the electronic device to measure the fluorescence by removing the skin visible reflection component caused by the second light source from the fourth image.

6. The electronic device of claim 1, wherein the compensation constant is stored in the memory of the electronic device.

7. The electronic device of claim 1, wherein the instructions, when executed by the processor, cause the electronic device to measure the fluorescence based on a fluorescence measurement request event.

8. The electronic device of claim 1, wherein the instructions, when executed by the processor, further cause the electronic device to diagnose a skin condition based on a fluorescence measurement value.

9. The electronic device of claim 1, further comprising a display, wherein the instructions, when executed by the processor, further cause the electronic device to control the display to display information indicating a result of diagnosing a skin condition.

10. A method of measuring fluorescence, the method comprising:

obtaining a compensation constant based on a difference between a first brightness corresponding to a first image captured while light of a first light source is emitted to a skin and a second brightness to a second image captured while light of a second light source is emitted to the skin;

applying the compensation constant to a third image captured while light of the first light source is emitted to the skin;

based on the third image to which the compensation constant is applied, obtaining a skin visible reflection component associated with an image which is captured while light of the second light source is emitted to the skin, the skin visible reflection component corresponding to a light component in the visible band that is emitted in addition to a light component in the ultraviolet (UV) band that is emitted while the light of the second light source is emitted to the skin; and measuring fluorescence by removing the skin visible reflection component from a fourth image captured while light of the second light source is emitted to the skin.

11. The method of claim 10, wherein the first light source comprises a visible light source, and wherein the second light source comprises a UV light source.

12. The method of claim 10, wherein the obtaining the compensation constant comprises:

emitting UV light to the skin by turning on the second light source;

emitting visible light to the skin by turning off the second light source and turning on the first light source;

obtaining a first skin reflectance map using a first R, G, B reflection distribution of the first image; and obtaining a second skin reflectance map using a second R, G, B reflection distribution of the second image, and wherein the compensation constant is obtained for each pixel position of the first image based on a difference between the first skin reflectance map and the second skin reflectance map.

13. The method of claim 10, wherein the compensation constant is obtained from a table, stored in a memory, associated with a plurality of compensation constants for each pixel position.

14. The method of claim 10, wherein the measuring the fluorescence comprises:

turning on the first light source;

obtaining the third image by capturing an image of the skin irradiated with visible light emitted by the first light source; and after the third image is obtained:

turning off the first light source, turning on the second light source, and obtaining the fourth image by capturing an image of the skin irradiated with UV light emitted by the second light source, wherein the obtaining the skin visible reflection component caused by the second light source comprises applying the compensation constant to the third image, and wherein the measuring the fluorescence further comprises removing the skin visible reflection component caused by the second light source from the fourth image.

15. The method of claim 10, further comprising:

storing the compensation constant in a memory of an electronic device.

16. The method of claim 10, further comprising:

measuring the fluorescence based on a fluorescence measurement request event.

17. The method of claim 16, further comprising:

diagnosing a skin condition based on a fluorescence measurement value.

18. The method of claim 17, further comprising:

displaying information indicating a result of diagnosing the skin condition on a display.

19. A non-transitory computer-readable storage medium storing instructions that when executed by at least one processor, cause the at least one processor to:

obtain a compensation constant based on a difference between a first brightness corresponding to a first image captured while light of a first light source is emitted to a skin and a second brightness corresponding to a second image captured while light of a second light source is emitted to the skin;

apply the compensation constant to a third image captured while light of the first light source is emitted to the skin;

based on the third image to which the compensation constant is applied, obtain a skin visible reflection component associated with an image which is captured while light of the second light source is emitted to the skin, the skin visible reflection component corresponding to a light component in the visible band that is emitted in addition to a light component in the ultraviolet (UV) band that is emitted while the light of the second light source is emitted to the skin; and measure fluorescence by removing the skin visible reflection component from a fourth image captured while light of the second light source is emitted to the skin.

20. The non-transitory computer-readable storage medium of claim 19, wherein the first light source comprises a visible light source, and wherein the second light source comprises a UV light source.

\* \* \* \* \*